United States Patent [19]

Nonami et al.

[11] Patent Number: 5,356,436

[45] Date of Patent: * Oct. 18, 1994

[54] MATERIALS FOR LIVING HARD TISSUE REPLACEMENTS

[75] Inventors: Tohru Nonami, Ichikawa; Hiroyasu Noma; Shinya Nakajima, both of Narashino, all of Japan

[73] Assignee: TDK Corporation, Tokyo, Japan

[ * ] Notice: The portion of the term of this patent subsequent to Jun. 30, 2009 has been disclaimed.

[21] Appl. No.: 872,949

[22] Filed: Apr. 21, 1992

Related U.S. Application Data

[62] Division of Ser. No. 533,768, Jun. 6, 1990, abandoned.

[30] Foreign Application Priority Data

Jun. 6, 1989 [JP] Japan .................................. 1-142058
Mar. 8, 1990 [JP] Japan .................................. 2-55126
May 23, 1990 [JP] Japan .................................. 2-131191

[51] Int. Cl.$^5$ ............................................... A61F 2/28
[52] U.S. Cl. .......................................... 623/16; 106/35; 623/901
[58] Field of Search .......................... 623/16, 66, 901; 106/35; 501/1, 123, 154; 433/228.1

[56] References Cited

U.S. PATENT DOCUMENTS

| 3,926,647 | 12/1975 | Wuhrer . | |
|---|---|---|---|
| 4,146,936 | 4/1979 | Aoyagi et al. | 623/18 |
| 4,352,890 | 10/1982 | Votava | 501/141 |
| 4,871,384 | 10/1989 | Kasuga | 65/30.1 |
| 5,125,971 | 6/1992 | Nonami et al. | 106/35 |

FOREIGN PATENT DOCUMENTS

0389713 10/1990 European Pat. Off. .
61-205637 9/1986 Japan .
2080281 2/1982 United Kingdom .

*Primary Examiner*—Randall L. Green
*Assistant Examiner*—Debra S. Brittingham
*Attorney, Agent, or Firm*—Oblon, Spivak, McClelland, Maier & Neustadt

[57] ABSTRACT

The materials for living hard tissue replacements of the present invention comprise a ceramic material which contain Cao and $SiO_2$ as essential components, and MgO as an optional components, are substantially free from calcium phosphate and are capable of forming a compound based on calcium phosphate by contact with an aqueous solution containing phosphorus, and show high biological affinity.

22 Claims, 3 Drawing Sheets

MATERIALS FOR LIVING HARD TISSUE REPLACEMENTS

This application is a division of application Ser. No. 07/533,768, filed on Jun. 6, 1990, now abandoned.

The present invention relates to a novel material for living hard tissue replacements. More particularly, it is concerned with a living hard tissue replacement not based on calcium phosphate, which has high strength and satisfactory acid resistance and exhibits surpassing biological activity and so is suitable as living hard tissue replacements such as artificial bones, dental roots and joints.

BACKGROUND OF THE INVENTION

Heretofore, metals such as stainless steel, metallic titanium and nickel/cobalt alloys and ceramic materials such as alumina and zirconia have been used as materials for living hard tissue replacements or implants such as artificial bones, dental roots, crowns and joints. For lack of assimilation to living tissue, however, they remain as useless xenobiotics in a living body after they have performed their duties. This causes an inconvenience in that such xenobiotics should be extracted and removed by surgical operations.

Calcium phosphate-based materials bearing resemblance to the composition of bones and teeth, on the other hand, assimilate to a living body with time and bond directly to the living tissue as time goes by. For that reason, no special operations are needed for the removal of them, since they cause no trouble even when remaining in the living body. Recently, ceramics based on calcium phosphate, composed primarily of apatite, tricalcium phosphate, bioglass or the like, have thus attracted attention as biologically active implant materials. However, such ceramics based on calcium phosphate has only limited use, since they are lower in mechanical strength than metals such as stainless steel and metallic titanium and ceramics based on metal oxides such as alumina and zirconia. In order to eliminate such disadvantages, various materials have been proposed, inclusive of sintered materials comprising calcium phosphate compounds containing alumina, silica and other metal oxides (Japanese Patent Publication 57(1982)-40803), crystal glass materials of high strength comprising tricalcium phosphate, apatite and diopside crystals (Japanese Patent Application Kokai No. 61(1986)-197446), materials in which hydroxyapatite is fused onto the surface of a core material having biological compatibility and strength (Japanese Patent Application Kokai No. 63(1988)-300754) and crystallized glass materials in which reinforcing components such as magnesia and silica are incorporated into a calcium phosphate-forming component (Japanese Patent Application Kokai No. 63(1988)-303830). As a premise, however, these materials should all be basically composed of calcium phosphate compounds of the same nature as bones and teeth so as to permit them to assimilate to in-vivo living tissue. This imposes some limitation upon the range of choice of composition, and often makes it impossible to achieve sufficient improvements in physical properties. Because of its solubility in a living system, $\beta$-tricalcium phosphate is likely to disintegrate before sufficient assimilation takes place. With the sintered materials in which reinforcing components such as alumina, silica and diopside are incorporated into calcium phosphate compounds, a similar problem is likely to arise, since they may be transformed into $\beta$-tricalcium phosphate.

It is thus desired to eliminate the drawbacks of such conventional living hard tissue replacements and implants.

SUMMARY OF THE INVENTION

An object of the present invention is to provide a novel material for living hard tissue replacements, which shows high mechanical strength and has improved biological affinity.

Making efforts in search of materials for living hard tissue replacements, the inventors have found that, upon coming into contact with body fluids, some ceramics making CaO and $SiO_2$ inevitable components form a compound based on calcium phosphate on the site of contact, showing satisfactory biological affinity, inter alia, biological activity, in spite of the the fact that they are ceramics or free from calcium phosphate. Such finding underlies the present invention.

More specifically, the present invention provides a material for living hard tissue replacements, which comprises a ceramic material which is substantially free from calcium phosphate in composition and contains CaO, $SiO_2$ and, if desired, MgO as essential components, and which is capable of forming a compound based on calcium phosphate by contact with a phosphorus-containing aqueous solution.

The material for living hard tissue replacements according to the present invention comprises a ceramic material which contains CaO and $SiO_2$ as its essential components and is substantially free from calcium phosphate in composition. In the ceramic material, the ratio of CaO to $SiO_2$ is between 1:4 and 6:1 by weight, preferably between 1:3 and 2:1 by weight. If that ratio departs from the above-defined range, there would then be a decrease in strength or biological affinity.

The ceramics used in the present invention may contain MgO in an amount no higher than 35% by weight based on the total weight. In general, the incorporation of MgO permits the sintering temperature to be decreased with improvements in the adhesion to bones.

BRIEF DESCRIPTION OF THE DRAWINGS

The above and other objects, features, and advantages of the present invention will be better understood from the following description taken in conjunction with the accompanying drawings, in which.

DETAILED DESCRIPTION OF THE INVENTION

The above-mentioned ceramics free from calcium phosphate may be obtained, for instance, starting from a binary system of CaO and $SiO_2$ and a ternary system of CaO, $SiO_2$ and MgO. In the case of the binary system, the proportion of the respective components is preferably 20 to 90% by weight for CaO and 10 to 80% by weight for $SiO_2$, based on the total weight. In the case of the ternary system, the proportion of the respective components is preferably 10 to 88% by weight for CaO, 10 to 80% by weight for $SiO_2$ and 2 to 35% by weight for MgO, more preferably 18 to 47% by weight for CaO, 37 to 68% by weight for $SiO_2$ and 10 to 25% by weight for MgO, based on the total weight.

The ceramics used in the present invention are characterized in that upon coming into contact with an aqueous solution containing phosphorus, for instance, pseudo or true body fluids., they form compounds based on calcium phosphate, e.g., hydroxyapatite on their surfaces of contact. Such a characteristic feature ensures that when they are implanted in a living system, a calcium phosphate-based, amorphous compound of satisfactory biological affinity is uniformly and rapidly precipitated on their surfaces of contact with living bones, so promoting the growth of newly grown bones. In addition, the thus formed junctions with living bones are very firm, since the components are contained in the implants in gradient concentrations with crystallographical continuity established between the implants and the living bones. With conventional implants comprising hydroxyapatite, however, the formation of newly grown bones is ununiform and slow, since any compound based on calcium phosphate is unlikely to be precipitated on their surface. Thus, newly grown bones to come into contact with the implants at an early stage are so limited in area that the junctions can be weak.

The composition of the ceramics used in the present invention may belong to the fields of diopside, wollastonite, alite, belite, akermanite, monticellite, forsterite, protoenstatite, tridymite and so on. Among others, preference is given to diopside, wollastonite, alite, halite, akermanite and monticellite, and by far the most preference is given to ceramics belonging chiefly to the diopside and wollastonite fields and capable of being sintered at relatively low temperatures of 1200° to 1350° C., because of their high biological affinity. It is noted that ceramics containing diopside, in particular, those belonging to the diopside field, have particularly high flexural strength and biological affinity.

Figure 1:
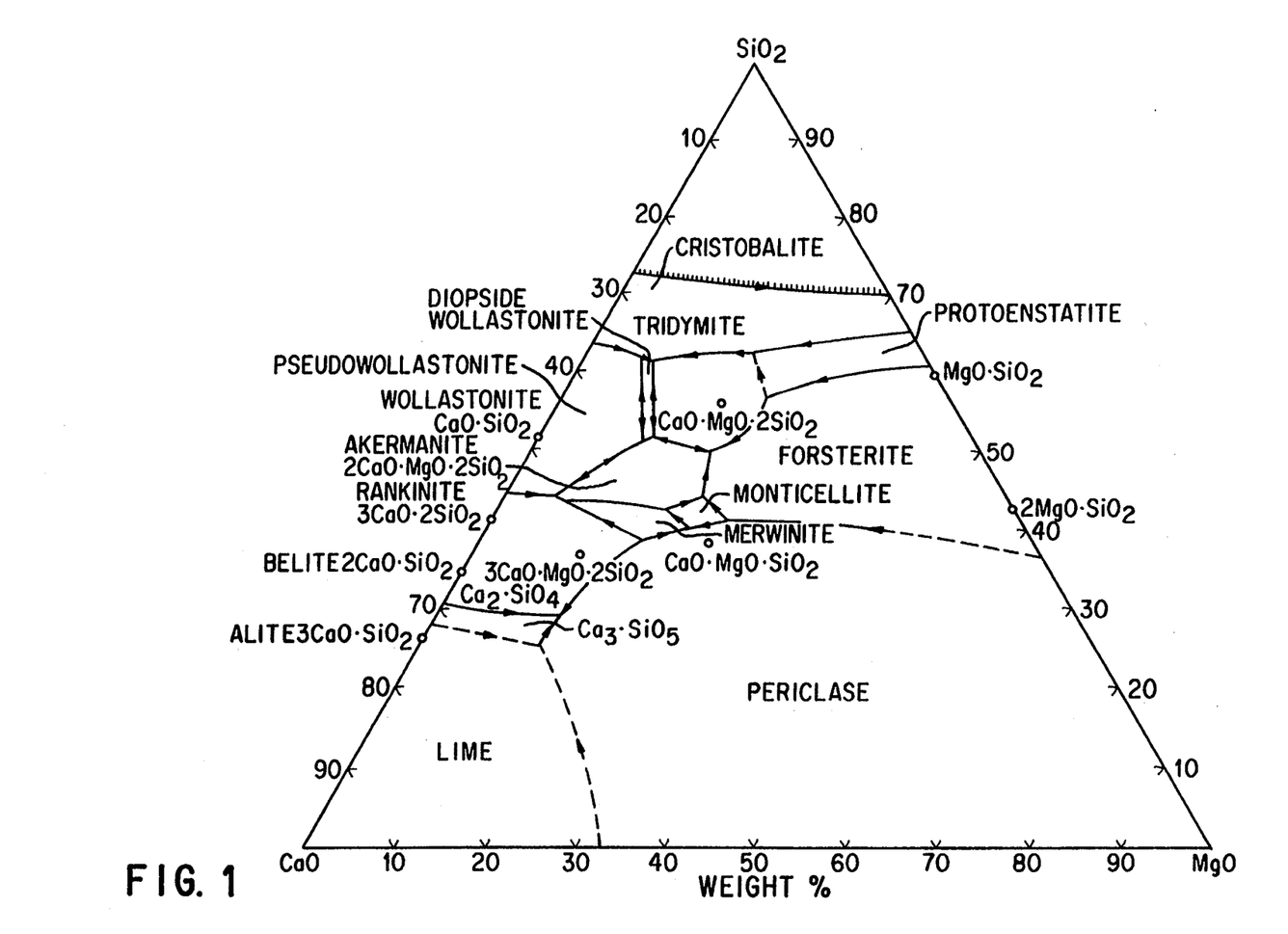
FIG. 1 is a compositional diagram for illustrating the composition of the ceramics according to the present invention.

FIG. 1 is a phase diagram of a $CaO-MgO-SiO_2$ system in which such ceramics as belonging to the diopside field are illustrated. Preferably, the phases of diopside ($CaO.MgO.2SiO$) and wollastonite ($CaO.SiO_2$), in particular, that of diopside, account for at least 40 vol %, esp., at least 50 vol %, more esp., 70 to 100 vol % of ceramics. The quantity of such phases contained in ceramic may easily be determined by X-ray powder diffraction methods.

In addition to the above-mentioned essential components, the ceramics of the present invention, if required, may contain any optional ingredients such as $Al_2O_3$, $TiO_2$, $Na_2O$, $K_2O$, $ZnO$ and $B_2O_3$ in such amounts that achieving the desired physical properties is not hindered, usually, in amounts of up to 5% by weight.

The ceramics used in the present invention may be obtained in conventional manners by mixing together calcium oxide and silicon oxide optionally with magnesium oxide at the required ratios, calcining or pre-sintering the mixture and then pulverizing the calcined product, followed by sintering. In place of such oxides, use may be made of substances capable of producing them under sintering conditions such as carbonates, bicarbonates and hydoxides of calcium and magnesium and silicic acid. Such stock materials may be used not only in powdery or granular form but also in slurry or solution form. Instead of using the stock materials corresponding to the individual components, use may be made of materials obtained by pulverizing diopside ($CaO\ 2SiO_2MgO$) prepared beforehand or compositions belonging to the diopside field. Alternatively, use may be made of mixtures of diopside with other like substances such as wollastonite, forsterite, akermanite, protoenstatite, tridymite and belite. Such mixtures are obtained as by-products when ceramics whose composition belongs to the diopside field are produced using any one of the feed stocks—calcium, magnesium and silicon oxides—in excess.

In order to prepare the materials for living hard tissue replacements according to the present invention, such stock materials for ceramics as mentioned above are powderized and well-mixed together in mixing machines such as ball mills, vibration mills, automatic mortars, mixers, juicers, sand mills and whipping units. Then, the mixture is dried at 50° to 300° C. for 10 minutes to 100 hours, followed by calcination or pre-sintering at 500° to 1600° C., preferably 800° to 1600° C. for 10 minutes to 200 hours. The thus obtained calcined product is pulverized and compacted into a desired shape by means of pressing, slip casting, etc., if required, with the addition of a binder such as polyvinyl alcohol. Finally, the compact is dried and sintered at a temperature ranging from 800° to 1600° C., preferably 1100° to 1550° C. In this case, the stock powders should have a BET size of usually at least 0.5 $m^2/g$, preferably at least 1 $m^2/g$, more preferably at least 3 $m^2/g$. The forming pressure used is 1 to 3000 $kg/cm^2$, and the sintering time is usually 10 minutes to 20 hours. Sintering is carried out at normal pressure but, if required, may be performed under pressures, usually selected from a range of 10 to 3000 $kg/cm^2$.

The materials for living hard tissue replacements according to the present invention may also be formed into a porous body including closed and open cells. When forming a porous body with the materials for living hard tissue replacements according to the present invention, high biological affinity is achievable because, owing to their strength being higher than that of conventional materials based on calcium phosphate, the range of pore diameter and porosity can be selected relatively freely. The formed porous body may usually have a pore diameter of 5 to 2000 $\mu m$, preferably 10 to 1000 $\mu m$ and a porosity of 10 to 80%, preferably 20 to 70% and more preferably 25 to 60%. The porous body may be prepared by incorporating thermally decomposable substances or organic fibers into the feed stock, followed by sintering, as hitherto applied in the production of porous ceramics. The thus obtained porous material has a compression strength of usually 10 MPa or higher, mostly 15 MPa or higher.

The materials for living hard tissue replacements according to the present invention may be employed either as blocks of the required shape or in the form of granules suitable for filling in a bone-deficient site.

In this case, the diameters of the granules may be selected from a range of usually 0.05 to 5 mm, preferably 0.1 to 3 mm, more preferably 0.1 to 2 mm, in consideration of the formation and strength of newly grown bones.

The material for living hard tissue replacements according to the present invention may be a composite body comprised of a substrate and a ceramic material free from calcium phosphate to be coated thereon.

No particular limitation is placed on the substrate for living hard tissue replacements or implants, if it is harmless to a living system and excels in strength. Used to this end are, for instance, metals such as Ti, W, Ni-Cr, Fe-Cr-Al, Ti-Zr, Fe-Ni-Cr, Mo, Ti-Al-V, Co-Cr-Mo, Ti-Mo, Co-Cr-N, stainless steel 304, 310 and 316; ceramics such as alumina, zirconia, silicon carbide, tungsten and silicon nitride; glass such as bioglass; plastics; and the like. Particular preference is given to pure Ti and titanium alloys in view of strength and stability.

The substrate for replacements or implants may be either densified throughout it or porous just like a sponge, with the surface smoothened. However, it should preferably be roughened on its surface by blasting, etching and other means to enhance the peel strength with respect to the coat layer. In the case of metal materials in particular, they may be cleaned on their surfaces by washing means such as water washing and ultrasonic washing. When it is required to provide an oxide film on the surface layers of metal materials, they may be either heat-treated in the air or in an atmosphere gas or oxidized with corrosive substances such as hydrochloric, sulfuric, nitric and oxalic acids.

In order to prepare the composite body, such a substrate as a metallic substrate is coated on its surface with a coating material by coating techniques so far available for the production of composite implants such as spray coating, solvent welding, solution coating and sputtering to provide thereon a coat layer of the above-mentioned ceramics free from calcium phosphate.

The substrate used should preferably be toughened on its surface by blasting or etching. Blasting may be carried out with, e.g., #20 to #400 steel shots. Spray coating may also be carried out to coat a similar material on the surface. In the case of metallic materials in particular, they may be oxidized on their surfaces by acid treatments. For the acid treatments, the metallic materials are coated with, or immersed in, corrosive inorganic and organic acids such as hydrochloric, sulfuric, nitric and oxalic acids. These treatments may be followed by a heat treatment at 300° to 1000° C. for 1 to 2 hours.

For spray coating used as the coating technique, plasma or a gas is usually used with a spray coating material having a particle size of #50 to 500. At a particle size less than #50, there would a drop of the flowability of particles during spray coating whereas, at higher than #500, difficulty would be encountered in depositing particles onto the substrate. Plasma should preferably be used, since the coating material of the present invention is more unlikely to change at high temperatures than hydroxyapatite. In plasma, hydroxyapatite tends to transform easily into tricalcium phosphate. For spray coating, the above-mentioned ceramics free from calcium phosphate according to the present invention is used in pulverized form.

For solvent welding, a paste obtained by mixing together the ceramics free from calcium phosphate and glass, both serving as coating materials, with water, etc. is coated on the substrate and welded thereto by sintering. The sintering temperature is not lower than the softening temperature of glass, usually 400° to 1000° C. The glass used may be based on, e.g., silica, borate, silicate, borosilicate and phosphate. Particular preference is given to glass based on borosilicate glass, with which welding treatments can be carried out at suitable temperatures. The amount of glass incorporated is 5 to 80% by weight, preferably 15 to 60% by weight based on the total weight of the coating materials. At less than 5% by weight the ability of the coating materials to be deposited onto the substrate would drop, whereas at higher than 80% by weight the biological affinity of the product would decrease.

For solution coating, a solution of the coating material dissolved in and saturated with a medium such as hydrochloric, sulfuric and nitric acids is used. The solution is coated onto the substrate, or the substrate is immersed in the solution, to provide a coat film on the substrate, which is then heated. The heating treatment is performed at a temperature of 300° C. or higher in an inert gas. At less than 300° C. the ability of the coating material to be deposited onto the substrate would drop, whereas at higher than 1000° C. the substrate to be used would be limited, since something in the substrate deteriorates. For sputtering, a target is mounted on a sputtering device for pre-sputtering for a certain time, and the substrate is then heated for substantial sputtering. The pre-sputtering time is usually 5 to 60 minutes, and the substantial sputtering time is determined depending upon the thickness of the film to be formed. The substantial sputtering is usually performed by heating at 20° to 500° C., followed by a post heat-treatment at 100° to 1300° C.

The layer coated on the composite body of the present invention has a thickness of 1 to 5000 $\mu$m, preferably 10 to 2000 $\mu$m, more preferably 20 to 1000 $\mu$m. At a thickness less than 1 $\mu$m the formation of newly grown bones would be less than satisfactory, whereas at a thickness exceeding 5000 $\mu$m the bond strength of the coat layer to the substrate would be reduced, giving rise to a relative decrease in the proportion occupied by the implant and so a drop of its mechanical strength. The prior art hydroxyapatite cannot possibly be treated at high temperatures and is so low in bond strength that even if a coat layer is provided on it to the thickness desired in the present invention, then that layer can peel off easily.

Preferably, the coat layer has a surface roughness of to 200 $\mu$m, particularly 5 to 100 $\mu$m. At less than 1 $\mu$m, it becomes so slippery that its bonding to bones can hardly take place. Nor is any anchoring effect virtually achievable. At a surface roughness exceeding 200 $\mu$m, on the other hand, its area of contact with bones is limited, giving rise to a reduction in its rate of bonding to bones.

The substrate and/or the coat layer may be formed into a porous body or bodies including closed and open cells. When forming a porous coat layer with the composite body according to the present invention, high biological affinity is achievable because, owing to its strength being higher than that of conventional materials based on calcium phosphate, a range of pore diameter and porosity can be selected relatively freely. The formed porous body may usually have a pore diameter of 5 to 2000 $\mu$m, preferably 10 to 1000 $\mu$m and a porosity of 10 to 80%, preferably 20 to 70% and more preferably 25 to 60%. The porous body may be prepared by incorporating thermally decomposable substances or organic fibers into the feed stock and coating the implant substrate with it, followed by sintering, as hitherto applied in the production of porous ceramics. The thus obtained porous coat layer has a compression strength of usually 10 MPa or higher, mostly 15 MPa or higher.

The material for living hard tissue replacements according to the present invention has strength and acid resistance comparable to those of biotic alumina. Moreover, that material adheres more rapidly to newly grown bones than do calcium phosphate-based implants such as β-tricalcium phosphate and hydroxyapatite, and forms uniform junctions.

With the material of the present invention, its junctions with biotic bones assume a low-crystalline or amorphous state, in which the components are present in continuous gradient concentrations so that as they approach the biotic bones, they assume a composition similar to that of the biotic bones. Thus, the present material offers various advantages such as providing firm junctures and being unlikely to suffer from fatigue.

Unlike hydroxyapatite, the ceramics forming the coat layer do not change to other substance even upon subject to heat treatments. This enables the treating temperature to be so elevated that its bonding strength with the implant substrate can be increased with increases in its own thickness and peel strength.

Thus, the material for living hard tissue replacements according to the present invention may be suitably used as artificial bones, dental roots and crowns and joints and for other purposes.

EXAMPLES

Examples of the present invention are given below by way of illustration and not by way of limitation.

The physical properties of samples including flexural strength and acid resistance were measured by the following procedures.

Relative Density

The density of a sintered sample was measured by the Archimedian method. The sintered sample was pulverized into powder having a surface area of 5 m$^2$/g which was measured for true density. Relative density (%) was calculated from the apparent and true densities.

Flexural Strength

Test specimens of 3×4×40 mm were cut out and mirror polished. They were measured by the three point bending test at a span of 36 mm and a cross head speed of 0.5 mm/min. (n = 10).

Compression Strength

Test specimens of 10×10×10 mm were cut out and measured with a compressive test machine at a cross head speed of 0.5 mm/min. (n=10).

Fracture Toughness Value (Kic)

Measured according to ASTM E399-83.

Crystal Grain Size

The average diameter was found from the area of a crystal grain determined under a scanning electron microscope (SEM for short), assuming that it was of a round shape.

Formation of Hydroxyapatite

Maintained at 37° C. were 150 ml of pseudo body fluids comprising an aqueous solution containing 142.0 mmol of Na$^+$, 5.0 mmol of K$^+$, 1.5 mmol of Mg$^{2+}$, 2.5 mmol of Ca$^{2+}$, 148.8 mmol of Cl$^-$, 4.2 mmol of HCO$_3^-$ and 1.0 mmol of HPO$_4^{2-}$, in which samples (6, each of 3 cm×4 cm×2 cm) were immersed. Seven days later, the precipitated phases were observed under SEMs and estimated on the following basis. It is noted that the components of each precipitated phase were determined by electron beam diffraction.

5: Precipitation took place all over the sample.
4: Precipitation took place nearly all over the sample, but did not partly.
3: Precipitation took place about half throughout the sample.
2: Precipitation took place slightly.
1: Precipitation took place hardly.
0: Precipitation did not take place at all.

Acid Resistance

A sample having a surface area of 200 mm$^2$ was placed in 200 cc of an aqueous solution of lactic acid at pH 4, and was permitted to stand for 48 hours, while the solution was maintained at 37° C. in a constant temperature bath and slightly shaken. Immediately thereafter, the sample under test was washed with water, dried, and estimated by determining its weight loss.

Examples 1-4 & Comparative Example 1

Powders of CaO, MgO and SiO$_2$, having an average particle size of 5 μm, were mixed together at a predetermined ratio, dried at 80° C. for 5 hours, and calcined at 950° C. for 5 hours. Then, the calcined product was pulverized, pressed at a pressure of 50 kg/cm$^2$ with the addition of 2% by weight of polyvinyl alcohol as a binder, and sintered at 1350° C. for 2 hours after five-hour drying at 80° C., obtaining implants with the composition shown in Table 1. The flexural strength and acid resistance of these implants are set forth together with those of hydroxyapatite.

Table 1 also shows the amounts, in % by volume, of the diopside phases contained, as measured by the X-ray powder diffraction method.

TABLE 1

|  | Input composition (wt %) | | | Diopside (vol %) | Flexural Strength (MPa) | Weight loss after acid resistance testing (%) |
| --- | --- | --- | --- | --- | --- | --- |
|  | CaO | MgO | SiO$_2$ |  |  |  |
| Example |  |  |  |  |  |  |
| 1 | 23.3 | 14.2 | 62.5 | 75 | 330 | 0.3 |
| 2 | 26.0 | 18.2 | 55.8 | 80 | 350 | 0.1 |
| 3 | 30.3 | 17.3 | 52.4 | 75 | 300 | 0.1 |
| 4 | 24.6 | 20.2 | 55.2 | 70 | 270 | 0.1 |
| Comparative Example |  |  |  |  |  |  |
| 1 | Hydroxyapatite | | | HAP 99 | 50 | 1.6 |

From the above results, it is found that the products according to the present invention are more unlikely to fracture and more durable—which means that they can stand up to long-term use—than the hydroxyapatite.

Observation of the formation of hydroxyapatite in the pseudo body fluids revealed that, three days later, the products according to the present invention all formed hydroxyapatite on their surfaces.

For the purpose of comparison, similar tests were carried out with alumina and titanium. Even after the lapse of ten days, however, no hydroxyapatite occurred at all.

Examples 5-14 & Comparative Examples 2-6

Similar procedures as in Examples 1-4 were repeated, but at varied feed input ratios and sintering temperatures, thereby obtaining implants with the composition shown in Table 2. The physical properties of the thus obtained ceramics are set forth in Table 2.

TABLE 2

| | Input composition | | | | | Sintering Temp. (°C.) | Ceramic physical properties | | | | | |
|---|---|---|---|---|---|---|---|---|---|---|---|---|
| | CaO (wt %) | SiO₂ (wt %) | MgO (wt %) | CaO SiO₂ | Composition* Field | | Crystal grain size (μm) | Phase composition*/ Amount (vol %) | Relative Density (%) | Flexural Strength (MPa) | KiC (MPam) | Formation of hydroxy-apatite |
| Example | | | | | | | | | | | | |
| 5 | 23.3 | 62.5 | 14.2 | 1/2.68 | D | 1230 | 2–3 | D/55 | 99.4 | 230 | 2.8 | 5 |
| 6 | 24.6 | 55.2 | 20.2 | 1/2.24 | D | 1270 | 3 | D/70 | 98.7 | 200 | 2.5 | 5 |
| 7 | 25.9 | 55.5 | 18.6 | 1/2.14 | D | 1270 | 2–3 | D/70 | 99.6 | 280 | 3.2 | 5 |
| 8 | 41.1 | 44.1 | 14.8 | 1/1.07 | A | 1300 | 4–5 | A/55 | 98.7 | 150 | 1.8 | 5 |
| 9 | 48.3 | 51.7 | — | 1/0.07 | W | 1420 | 4–5 | W/60 | 94.0 | 250 | 2.2 | 5 |
| 10 | 73.7 | 26.3 | — | 2.8/1 | AL | 1480 | 5 | AL/60 | 96.8 | 180 | 1.9 | 4 |
| 11 | 65.1 | 34.9 | — | 1.86/1 | B | 1450 | 5 | B/65 | 94.5 | 180 | 1.9 | 4 |
| 12 | 33.0 | 42.5 | 24.5 | 1/1.29 | M | 1400 | 6 | M/55 | 91.0 | 130 | 1.2 | 4 |
| 13 | 85.5 | 14.5 | — | 5.9/1 | L | 1550 | 5–10 | AL | 89.5 | 80 | 0.8 | 3 |
| 14 | 29.0 | 40.4 | 30.6 | 1/3.9 | P | 1580 | 7–15 | W. A | 80.0 | 40 | 0.4 | 3 |
| Comparative Example | | | | | | | | | | | | |
| 2 | — | 59.9 | 40.1 | — | F | 1470 | 7 | F/50 | 91.0 | 130 | 1.2 | 0 |
| 3 | Al₂O₃ 100.0 | | | — | Al₂O₃ | 1550 | 3–4 | Al₂O₃/99 | 99.0 | 300 | 3.0 | 0 |
| 4 | 55.8 | P₂O₅ = 42.4 | | — | HAP | 1350 | 1–2 | HAP/99 | 99.8 | 100 | 1.1 | 0 |
| 5 | 54.2 | P₂O₅ = 45.8 | | — | TCP | 1400 | 2–3 | TCP/99 | 99.0 | 100 | 0.9 | 0 |
| 6 | — | 100 | — | — | Silica glass | 1500 | — | Silica glass/99 | 99.8 | 100 | 0.6 | 0 |

*D: diopside  W: wollastonite  A: akermanite  Al: alite  F: fosterite  L: Lime  P: Periclase  B: Belite  M: monticellite  HAP: hydroxyapatite  TCP: Tricalcium phosphate From Table 2, it is found that the prior art implants are incapable of forming hydroxyapatite, but the implants according to the present invention are all well capable of forming hydroxyapatite.

Examples 15–34 & Comparative Examples 7–10

Crystalline cellulose as a thermally decomposable substance was added in the amount shown in Table 3 to a powdery mixture of given amounts of CaO, SiO₂ and MgO, which was then dried at 70° C. for 5 hours. Thereafter, the dried products were calcined and sintered at the temperatures specified in Table 3, obtaining porous implants in granular and block forms. The physical properties of the implants obtained are shown in Table 3 (for granules) and Table 4 (for blocks).

Biological affinity tests were performed as follows.

The porous implants were filled in holes of 3×4×6 mm formed in the lower edge of the jaw bone of each adult, masculine rabbit, weighing 2.5 to 2.8 kg.

Polished, but non-decalsified specimens were prepared after the lapse of six week from the operations. An SEM photomicrograph was taken on the interface between the implant and the newly grown bone, and evaluation was made according to the following ratings.

a: The newly grown bone adhered completely to the implant with the pores filled up.
b: Half or more of the newly grown bone adhered to the implant with half or more of the pores filled up.
c: Half or more of the newly grown bone adhered to the implant with the pores filled partly.
d: The newly grown bone adhered partly to the implant with the pores filled partly.

TABLE 3

| | Input Composition | | | | | Thermally decomposable substance (wt %)* | Sintering condition | |
|---|---|---|---|---|---|---|---|---|
| | CaO (wt %) | SiO₂ (wt %) | MgO (wt %) | CaO SiO₂ | Composition Field | | Pre-sintering (°C.) | Substantial sintering (°C.) |
| Example | | | | | | | | |
| 15 | 25.9 | 55.5 | 18.6 | 1/2.14 | D | 50 | 1200 | 1250 |
| 16 | 25.9 | 55.5 | 18.6 | 1/2.14 | D | 35 | 1200 | 1250 |
| 17 | 25.9 | 55.5 | 18.6 | 1/2.14 | D | 20 | 1200 | 1250 |
| 18 | 25.9 | 55.5 | 18.6 | 1/2.14 | D | 70 | 1200 | 1250 |
| 19 | 25.9 | 55.5 | 18.6 | 1/2.14 | D | 45 | 1200 | 1250 |
| 20 | 23.3 | 62.5 | 14.2 | 1/2.68 | D | 30 | 1100 | 1200 |
| 21 | 23.3 | 62.5 | 14.2 | 1/2.68 | D | 70 | 1100 | 1200 |
| 22 | 25.9 | 55.5 | 18.4 | 1/2.14 | D | 40 | 1200 | 1250 |
| 23 | 25.9 | 55.5 | 18.4 | 1/2.14 | D | 45 | 1200 | 1250 |
| 24 | 25.9 | 55.5 | 18.4 | 1/2.14 | D | 95 | 1200 | 1250 |
| 25 | 43.4 | 41.8 | 14.8 | 1/0.96 | A | 35 | 1350 | 1300 |
| 26 | 73.0 | 27.0 | — | 1/0.37 | AL | 30 | 1450 | 1420 |
| Comparative Example | | | | | | | | |
| 7 | 55.8 | P₂O₅ = 42.4 | — | | HAP | 40 | 900 | 1350 |
| 8 | 54.2 | P₂O₅ = 45.8 | — | | TCP | 35 | 900 | 1350 |

| | Ceramic physical properties | | | | | |
|---|---|---|---|---|---|---|
| | Grain size (mm) | Phase composition/ Amount (vol %) | Pore diameter (μm) | Porosity (%) | Relative density (%) | Compression strength (MPa) | Biological affinity |

TABLE 3-continued

| Example | | | | | | | | |
|---|---|---|---|---|---|---|---|---|
| 15 | 0.2 | D/65 | 10 | 45 | 99.6 | 20 | a | |
| 16 | 1.5 | D/65 | 50 | 30 | 99.6 | 30 | a | |
| 17 | 4.0 | D/65 | 7 | 15 | 99.6 | 45 | b | |
| 18 | 4.0 | D/65 | 120 | 65 | 99.6 | 15 | a | |
| 19 | 0.5 | D/65 | 20 | 40 | 99.6 | 25 | a | |
| 20 | 0.4 | D/55 | 15 | 25 | 99.0 | 25 | a | |
| 21 | 4.0 | D/55 | 350 | 65 | 99.0 | 15 | a | |
| 22 | 6.0 | D/65 | 20 | 35 | 99.6 | 25 | c | |
| 23 | 2.0 | D/65 | 4 | 40 | 99.6 | 55 | c | |
| 24 | 0.5 | D/65 | 25 | 90 | 99.6 | 9 | b | |
| 25 | 0.3 | A/55 | 20 | 30 | 98.1 | 15 | b | |
| 26 | 0.5 | AL/60 | 15 | 25 | 99.8 | 10 | b | |
| Comparative Example | | | | | | | | |
| 7 | 0.2 | HAP/99 | 15 | 35 | 99.8 | 8 | d | |
| 8 | 0.3 | TCP/99 | 20 | 30 | 99.8 | 9 | d | |

*Ratio based on the total weight of powder mixture

TABLE 4

| | Input Composition | | | | | Sintering condition | |
|---|---|---|---|---|---|---|---|
| | CaO (wt %) | $SiO_2$ (wt %) | MgO (wt %) | CaO/$SiO_2$ | Composition Field | Thermally decomposalble substance (wt %)* | Pre-sintering (°C.) | Substantial sintering (°C.) |
| Example | | | | | | | | |
| 27 | 25.9 | 55.5 | 18.6 | 1/2.14 | D | 55 | 1200 | 1250 |
| 28 | 25.9 | 55.5 | 18.6 | 1/2.14 | D | 60 | 1200 | 1250 |
| 29 | 25.9 | 55.5 | 18.6 | 1/2.14 | D | 55 | 1200 | 1250 |
| 30 | 24.6 | 55.2 | 20.2 | 1/2.24 | D | 80 | 1200 | 1250 |
| 31 | 25.9 | 55.5 | 18.6 | 1/2.14 | D | 15 | 1200 | 1250 |
| 32 | 25.9 | 55.5 | 18.6 | 1/2.14 | D | 60 | 1200 | 1250 |
| 33 | 25.9 | 55.5 | 18.6 | 1/2.14 | D | 95 | 1200 | 1250 |
| 34 | 48.3 | 51.7 | — | 1/1.07 | W | 65 | 1450 | 1420 |
| Comparative Example | | | | | | | | |
| 9 | 55.8 | $P_2O_5$ = 42.4 | — | — | HAP | 50 | 900 | 1350 |
| 10 | 54.2 | $P_2O_5$ = 45.8 | — | — | TCP | 60 | 900 | 1350 |

| | Ceramic physical properties | | | | |
|---|---|---|---|---|---|
| | Phase composition/ Amount (vol %) | Pore diameter (μm) | Porosity (%) | Relative Density (%) | Compression strength (MPa) | Biological affinity |
| Example | | | | | | |
| 27 | D/65 | 50 | 50 | 99.6 | 25 | a |
| 28 | D/65 | 300 | 55 | 99.6 | 15 | a |
| 29 | D/65 | 10 | 45 | 99.6 | 35 | b |
| 30 | D/70 | 50 | 75 | 99.6 | 10 | a |
| 31 | D/65 | 50 | 10 | 99.6 | 50 | c |
| 32 | D/65 | 3 | 55 | 99.6 | 55 | c |
| 33 | D/65 | 100 | 90 | 99.6 | 8 | b |
| 34 | W/65 | 100 | 60 | 95.0 | 15 | a |
| Comparative Example | | | | | | |
| 9 | — | 30 | 45 | 99.6 | 9 | d |
| 10 | — | 25 | 55 | 99.0 | 8 | d |

*Ratio based on the total weight of powder mixture

As is evident from Tables 3 and 4, the implants according to the present invention, even if made porous, have strength and biological affinity more improved than those of implants based on calcium phosphate such as hydroxapatite and tricalcium phosphate, so that they can adhere more firmly to newly grown bones.

Example 35

The diopside obtained in Ex. 5 (Sample A), hydroxyapatite containing 20% by weight of a diopside composition (Sample B) and hydroxyapatite (Sample C) were each formed into a block measuring 3×4×6 mm, which was then implanted in the lower edge of the jaw bone of an adult, masculine rabbit weighing 2.5 to 2.8 kg for the observation of recuperation.

Two weeks later, the samples all showed a sign of forming newly grown bones. However, the block sample A, as a whole, came in close contact with the newly grown bone, whereas the block samples B and C were each found to have only a part brought into direct contact with the newly grown bone, leaving behind substantial gaps.

Four weeks after the operations, the layer structure of the part of the block sample A contacting the newly grown bone was found to increase in thickness. In the samples B and C, however, there was no change in the thickness of the layer structures of their parts of contact.

Twenty-four weeks later, whatever the samples, there was integration of the newly grown bones with the matrix bones with no appreciable boundary therebetween. In the case of Samples B and C, however, the sequence of the bone cells was in parallel with them, differing quite from that of the matrix bones. In the case of Sample A, on the other hand, the sequence of the bone cells was entirely coincident with that of the matrix bone and there was no difference at all in the junction with the bone between its part bonded to the matrix bone and its outer periosteal part.

Figure 2:
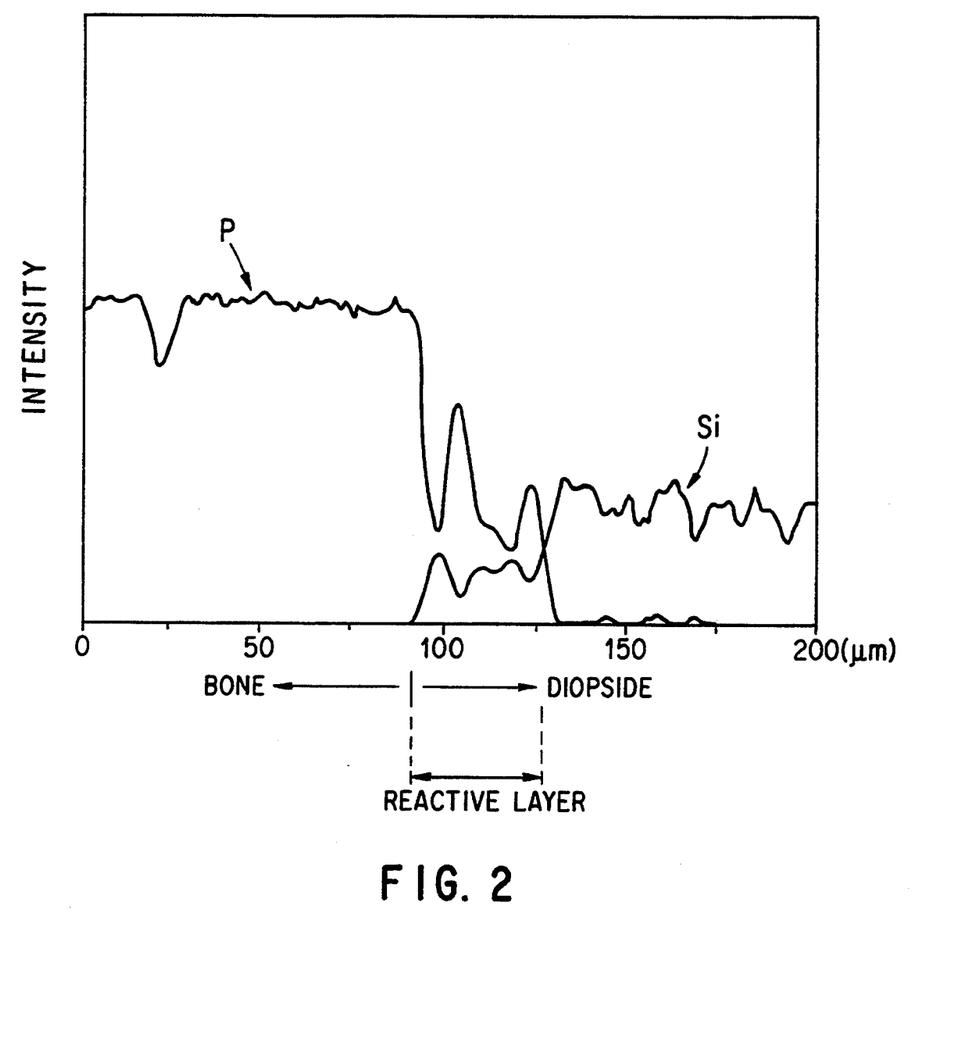
FIG. 2 is an EPMA analysis graph showing a gradient of concentration of the components of an implant according to the present invention at its junction with the matrix bone, when it is implanted in the body of a rabbit.

FIG. 2 is an EPMA spectral diagram showing a change of the composition across the junction of the diopside sample A with the matrix bone after 24 weeks, from which it is seen that the components of an intermediate layer occurring between the newly grown bone and the diopside have a gradient of concentration.

Figure 3:
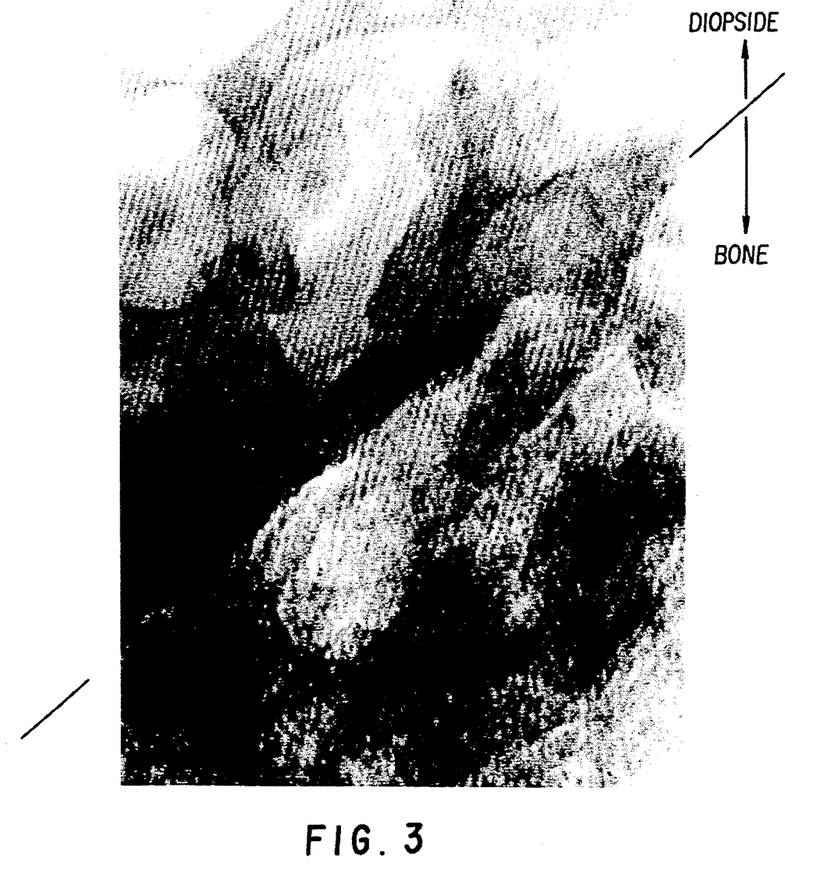
FIG. 3 is a TEM photomicrograph showing the sequence of the crystal structure at the same junction.

FIG. 3 is a high-resolution photomicrograph taken on the junction between the sample A and the matrix bone with a transmission electron microscope after 24 weeks, from which it is seen that the sequences of the bone cells are entirely identical with each other on the diopside and matrix bone sides with little or no boundary between them.

Examples 36 & Comparative Example 11

A columnar Ti piece of 5 mm in diameter and 10 mm in height was blasted with 100-mesh steel, followed by acetone-washing. By plasma spray coating, the thus prepared substrate was coated with diopside having a particle size of 150 to 250 mesh at a voltage of 60 V and 500 A in a gas mixture of argon/hydrogen (5:1), obtaining a composite implant having a firm diopside coat layer of 100 μm in thickness, which was then implanted in the jaws of a rabbit. Twenty-four weeks later, the coat layer was found to bond firmly to the bone with neither peeling nor "dissolving-out".

For the purpose of comparison, a similar coat layer of 100 μm in thickness was prepared using hydroxyapatite in place of the diopside. That coat layer was found to contain tricalcium phosphate.

As a result of similar implantation testing, this hydroxyapatite was found to bond partly to the bone and "dissolve out" and peel off partly.

Thus, it is understood that the composite implant according to the present invention has improved biological affinity.

Examples 37–42 & Comparative Example 12

In similar manners as set forth in Examples 5–14, powders selected from CaO, MgO, SiO$_2$ and P$_2$O$_3$ were mixed together in the ratios specified in Table 5, dried, and calcined at 950° C. for 5 hours. Then, the calcined product was pulverized and compacted or granulated with the addition of 2% by weight of polyvinyl alcohol as a binder, followed by drying at 80° C. for 5 hours. The dried product was subsequently sintered at the temperatures specified in Table 5 for 2 hours, thereby obtaining ceramics having the same composition as the input composition, as set forth in Table 5.

With thus obtained composite implants, the following peeling and HAP-forming experiments were carried out. The results are summarized in Table 5.

Releasability

The samples were scratched with angles of CaF$_2$ fluorite having a Mohs hardness of 4, and the results were estimated on the following basis.
O: No powder fell off.
Δ: Powders fell off.
X: The coat layer was streaked.
: The coat layer peeled off.

From Table 5, it was ascertained that the materials of the present invention, if formed into composite implants, were well capable of forming HAP and gave similar results.

In addition, it was understood that the composite implants of the present invention excelled in peeling strength.

It is noted that the amounts of diopside, etc. in Examples 37–42 were virtually identical with those in Examples 5-14.

TABLE 5

| | Input composition | | | | | Sintering | | | |
|---|---|---|---|---|---|---|---|---|---|
| | CaO (wt %) | SiO$_2$ (wt %) | MgO (wt %) | P$_2$O$_5$ (wt %) | Composition* Field | Temp. (°C.) | Thickness (μ) | Releasability | Formation of HAP |
| Example | | | | | | | | | |
| 37 | 23.3 | 62.5 | 14.2 | — | D | 1230 | 150 | ○ | 5 |
| 38 | 25.9 | 55.5 | 18.6 | — | D | 1230 | 100 | ○ | 5 |
| 39 | 41.1 | 44.1 | 14.8 | — | A | 1300 | 130 | ○ | 5 |
| 40 | 48.3 | 51.7 | — | — | W | 1420 | 130 | ○ | 5 |
| 41 | 73.7 | 26.3 | — | — | AL | 1480 | 150 | Δ | 4 |
| 42 | 65.1 | 34.9 | — | — | B | 1450 | 150 | Δ | 4 |
| Comparative Example | | | | | | | | | |
| 12 | 55.8 | — | — | 42.5 | HAP | 1350 | 130 | x | 0 |

*D: diopside  A: akermanite  W: wollastonite  AL: alite  B: Belite  HAP: hydroxyapatite Examples 43 & Comparative Example 13

A substrate similar to that of Ex. 36 was coated with a mixture of diopside powders (with a BET of 10), Na$_2$O.B$_2$O$_3$-SiO$_2$ (43:7:50) glass and water (with a glass content of 25%), and was then sintered at 800° C. for 60 minutes to obtain a composite implant provided with a coat layer of 150 μm in thickness.

For the purpose of comparison, another composite implant having a coat layer of 100 μm in thickness was obtained in similar manners as mentioned above, provided that HAP was used in lieu of the diopside.

However, that coat layer partly contained TPC.

As a result of implantation tests performed in similar manners as described in Ex. 36 and Comp. Ex. 11, Example 43 were found to be superior to Comparison Example 13 in the area of direct adhesion to the bone.

Example 44 & Comparative Example 14

An implant substrate similar to that of Ex. 36 was immersed in 25% sulfuric acid for 60 seconds, sintered at 550° C. for 120 minutes, coated with a solution of 2 g of diopside dissolved in 10 ml of a 30% aqueous solution of nitric acid, and was finally sintered at 500° C. for 30 minutes in argon. This operation cycle was repeated four times to obtain a composite implant provided with a firm diopside coat layer of 200 μm in thickness.

Another composite implant having a coat layer of 200 μm in thickness was obtained in similar manners as mentioned above, provided that HAP was used for the diopside.

As a result of implantation tests performed with these implants in similar manners as in Example 36 and Comparative Example 11, Example 44 was found to be superior to Comparative Example 14 in the area of direct adhesion to the bone.

Example 45 and & Comparative Example 15

An implant substrate similar to that of Ex. 36 was immersed in concentrated sulfuric acid for 120 seconds and then in boron sodium hydride for a further 30 seconds, sintered at 600° C. for 20 minutes, coated with a solution of 2 g of diopside dissolved in 10 ml of a 20% aqueous solution of nitric acid, and was finally sintered at 1300° C. for 120 minutes in argon. This operation cycle was repeated four times to obtain a composite implant provided with a firm diopside coat film of 50 μm in thickness.

For the purpose of comparison, another composite implant having a coat layer of 50 μm in thickness was obtained in similar manners as mentioned above, provided that HAP was used for the diopside. These implants were found to be similar in properties to those of Ex. 44 and Comp. Ex. 14.

Example 46

With a target of sintered diopside, an implant substrate similar to that of Ex. 36 was sputtered at a total pressure of $8.4 \times 10^{-5}$ Torr and a preset pressure of $1.0 \times 10^{-2}$ Torr for a pre-sputtering time of 30 minutes and a substantial sputtering time of 90 minutes, thereby obtaining a composite implant provided with a single diopside coat layer of 1 μm in thickness. Again, this had improved biological affinity.

Example 47 and Comparative Example 16

A columnar T1 piece of $10 \times 100 \times 100$ mm was blasted with 200-mesh steel, followed by acetone-washing. By plasma spray coating, the thus prepared substrate was coated with diopside having a particle size of 200 to 300 mesh at a voltage of 60 V and 500 A in a gas mixture of argon/hydrogen (5:1), obtaining a firm diopside coat layer of 3800 μm in thickness. No surface exfoliation occurred even by Mohs testing at a hardness of 4.

For the purpose of comparison, an HAP coat layer of the same thickness was obtained in similar manners as mentioned above. This coat layer, containing PTC, suffered from surface exfoliation by Mohs testing at a hardness of 4.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for replacement of living hard tissue comprising:
   providing an implant comprising a ceramic material which contains at least 40% by volume of a diopside composition, a wollastonite composition or a mixture of diopside and wollastonite compositions, and which (i) contains CaO and $SiO_2$ as essential components, (ii) is substantially free from calcium phosphate and (iii) is capable of forming a compound based in calcium phosphate by contact with an aqueous solution containing phosphorous, said CaO and $SiO_2$ being present in a weight ratio of CaO to $SiO_2$ of between 1:4 and 6:1; and
   inserting said implant into a living body to replace living hard tissue.

2. The process as claimed in claim 1, wherein said ceramic material contains MgO in addition to the essential components of CaO and $SiO_2$.

3. The process as claimed in claim 2, wherein said ceramic material contains 10 to 88% by weight of CaO, 10 to 80% by weight of $SiO_2$ and 2 to 35% by weight of MgO.

4. The process as claimed in claim 3, wherein said ceramic material contains 18 to 47% by weight of CaO, 37 to 68% by weight of $SiO_2$ and 10 to 25% by weight of MgO.

5. The process as claimed in claim 1, wherein said ceramic material contains at least 40% by volume of a diopside composition.

6. The process as claimed in claim 1, wherein said ceramic material contains at least 50% by volume of a diopside composition, a wollastonite composition or a mixture of diopside and wollastonite compositions.

7. The process as claimed in claim 6, wherein said ceramic material contains 70% to 100% by volume of a diopside composition, a wollastonite composition or a mixture of diopside and wollastonite compositions.

8. The process as claimed in claim 1, wherein said implant comprises a substrate having a coat layer of said ceramic material on a surface thereof.

9. The process as claimed in claim 8, wherein said coat layer has a thickness of 1 to 5000 gm.

10. The process as claimed in claim 1, wherein said coat layer has a thickness of 10 to 2000 μm.

11. The process as claimed in claim 10, wherein said coat layer has a thickness of 20 to 1000 μm.

12. The process as claimed in claim 8, wherein said coat layer has a surface roughness of 1 to 200 μm.

13. The process as claimed in claim 12, wherein said coat layer has a surface roughness of 5 to 100 μm.

14. The process as claimed in claim 8, wherein said coat layer is porous.

15. The process as claimed in claim 8, wherein said substrate comprises metal, ceramic, glass or plastic.

16. The process as claimed in claim 6, wherein said substrate comprises a metal selected from the group consisting of Ti, W, Ni-Cr alloy, Fe-Cr-Al alloy, Ti-Zr alloy, Fe-Ni-Cr alloy, Mo, Ti-Al-V alloy, Co-Cr-Mo alloy, Ti-Mo alloy, Co-Cr-Ni alloy, stainless steel 304, stainless steel 310 and stainless steel 316.

17. The process as claimed in claim 6, wherein said substrate comprises Ti or an alloy thereof.

18. The process as claimed in claim 6, wherein said substrate comprises a ceramic selected from the group consisting of alumina, zirconia, silicon carbide, tungsten nitride and silicon nitride.

19. The process as claimed in claim 1, wherein said implant is a porous body of said ceramic material having a pore diameter of 5 to 2000 μm and a porosity of 10 to 80%.

20. The process as claimed in claim 19, wherein said porous body has a pore diameter of 10 to 1000 μm.

21. The process as claimed in claim 19, wherein said porous body has a porosity of 20 to 70%.

22. The process as claimed in claim 21, wherein said porous body has a porosity of 25 to 60%.

* * * * *